United States Patent [19]

Strunk et al.

[11] Patent Number: 4,804,653

[45] Date of Patent: Feb. 14, 1989

[54] THIOMETHYL-SUBSTITUTED ORGANOSILANE COMPOUNDS AND THEIR USE AS PESTICIDES

[75] Inventors: Richard J. Strunk, Cheshire; Richard C. Moore, Wallingford, both of Conn.

[73] Assignee: Uniroyal Chemical Company, Inc., Middlebury, Conn.

[21] Appl. No.: 859,158

[22] Filed: May 2, 1986

[51] Int. Cl.$^4$ .......................... A01N 55/00; C07F 7/10
[52] U.S. Cl. .......................... 514/63; 546/14; 549/4; 549/214; 556/423; 556/427
[58] Field of Search .......................... 546/14; 514/63; 549/214, 4; 556/423, 427

[56] References Cited

U.S. PATENT DOCUMENTS

| | | | |
|---|---|---|---|
| 3,532,733 | 10/1970 | Lee | 556/427 |
| 4,397,864 | 8/1983 | Nakatani et al. | 549/445 |
| 4,434,161 | 2/1984 | Barcza | 514/63 |

FOREIGN PATENT DOCUMENTS

| | | | |
|---|---|---|---|
| 94085 | 11/1983 | European Pat. Off. | 546/290 |
| 1983232513 | 7/1985 | Japan | 556/489 |
| 2120664A | 12/1983 | United Kingdom | 546/290 |

OTHER PUBLICATIONS

"A New Type of Synthetic Pyrethroid Insecticide", by T. Udagawa et al., *Recent Advances in the Chemistry of Insect Control*, pp. 192–204, N. F. Janes, Ed., Royal Society of Chemistry (1980).

*Primary Examiner*—Robert T. Bond
*Attorney, Agent, or Firm*—William E. Dickheiser

[57] ABSTRACT

Thiomethyl-substituted organosilane compounds demonstrate unexpected insecticidal and acaricidal control. Also disclosed are compositions comprising such compounds, a method of controlling pests employing such compounds, and a process of manufacturing such compounds.

16 Claims, No Drawings

THIOMETHYL-SUBSTITUTED ORGANOSILANE COMPOUNDS AND THEIR USE AS PESTICIDES

FIELD OF THE INVENTION

This invention is directed to thiomethyl-substituted organosilane compounds which exhibit insecticidal and acaricidal activity. In other aspects, this invention relates to pesticidal compositions comprising such compositions as well as to methods of making and using such compounds.

BACKGROUND OF THE INVENTION

The destructive effects of mites and insects upon crops needs no elucidation. Although many compounds have been developed for the control of these pests, it would nevertheless be desirable to possess additional compounds which would effectively control such pests.

U.S. Pat. No. 4,397,864 to K. Nakatani et al discloses 2-arylpropyl ether and thioether derivatives, having utility for insecticidal and acaricidal applications, which compounds are of the formula:

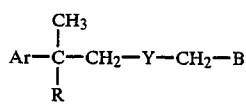

wherein Ar is aryl, R is methyl or ethyl, Y is oxygen or sulfur and B is:

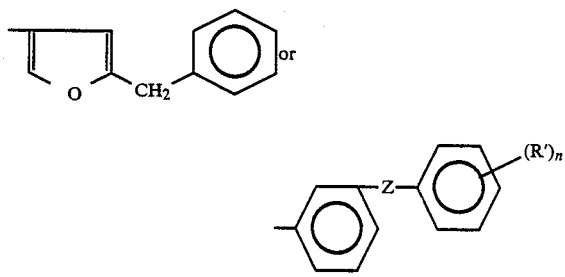

wherein Z is oxygen, sulfur, carbonyl or methylene; R' is hydrogen, halogen, lower alkyl; or lower alkoxy; and n is an integer of 1–5; R' being the same or different when n is 2 or more.

European Patent Application No. 94,085 to S. Nishidi et al discloses ether compounds useful as active ingredients in insecticidal and/or acaricidal compositions, which compounds are of the formula:

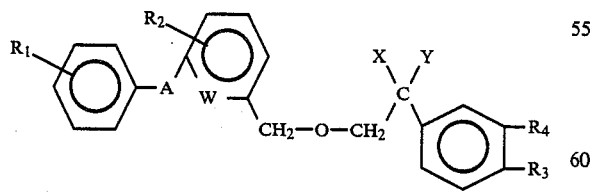

wherein: W is methine or nitrogen; $R_1$ is hydrogen, halogen or methyl; $R_2$ is hydrogen or fluorine; $R_3$ and $R_4$ are the same or different and may be hydrogen, halogen, $C_1$–$C_4$ alkyl, $C_1$–$C_4$ alkoxy, difluoromethoxy, 2,2,2-trifluoroethoxy or, taken together, are 3,4-methylenedioxy; A is oxygen, methyl or imino; and X and Y are hydrogen or methyl or, taken together, are ethylene or 1,1-difluoroethylene.

U.K. Patent Application GB No. 2120664A, K. Nakatani et al, discloses insecticidal and acaricidal compounds having the formula:

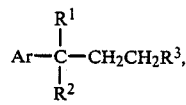

wherein: Ar is substituted or unsubstituted phenyl or naphthyl; $R^1$ is methyl, ethyl or isopropyl; $R^2$ is hydrogen or methyl, or $R^1$ and $R^2$ together with the carbon to which they are attached jointly represent a substituted or unsubstituted cycloalkyl; and $R^3$ is a fundamental group of an alcohol usually used in the form $R^3$OH as to natural or synthetic pyrethroids. Such compounds are prepared by reacting a ketone with an aldehyde compound to produce an alpha,beta-unsaturated carbonyl compound which then is reduced to provide the above-described aromatic alkane derivative.

"A New Type of Synthetic Pyrethroid Insecticide", by T. Udagawa et al, *Recent Advances In The Chemistry Of Insect Control*, pages 192–204, N. F. Janes, Ed., Royal Society of Chemistry (1980) shows pyrethroid-like insecticides of the formula:

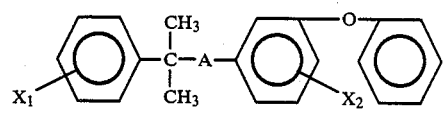

wherein: A is alkyl ether, alkenylene or alkylene; $X_2$ is hydrogen or fluorine; and $X_1$ is hydrogen, chlorine, methyl, methoxy, ethoxy or difluoromethoxy. Specifically disclosed are 2-(4-ethoxyphenyl)-2-methylpropyl 3-phenoxybenzyl ether, and 1-(3-phenoxy-4-fluorophenyl)-4-(4-ethoxyphenyl)-4-methylpentane. The insecticidal efficacy of various $X_1$ and $X_2$-substituted methylpentane compounds is also shown.

DESCRIPTION OF THE INVENTION

In one aspect, this invention is directed to a compound of the formula:

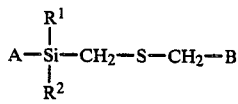

[I]

wherein:
$R_1$ and $R_2$ may be the same or different, and are lower alkyl;
A is selected from radicals having the structure:

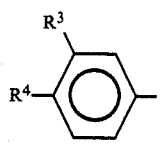

(i)

wherein $R^3$ and $R^4$ are the same or different and are hydrogen $C_1$–$C_4$ alkyl, $C_1$–$C_4$ alkoxy, $C_1$–$C_4$ haloalkyl, $C_1$–$C_4$ haloalkoxy, halo, phenyl, phenoxy or $C_1$–$C_4$ alkylthio; or wherein $R^3$ and $R^4$ taken together are methylenedioxy;

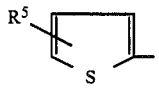

(ii)

wherein $R^5$ is hydrogen, chlorine, bromine or $C_1$-$C_4$ alkyl; and

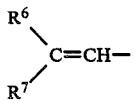

(iii)

wherein $R^6$ and $R^7$ are the same or different and are hydrogen, fluorine, chlorine, bromine or trifluoromethyl; and B is selected from radicals having the structure:

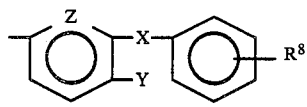

(i)

wherein:
X is oxygen, NH, $CH_2$, carbonyl or sulfur;
Y is hydrogen, fluorine, chlorine or methyl;
Z is CH or nitrogen; and
$R^8$ is hydrogen, fluorine, chlorine or bromine; and

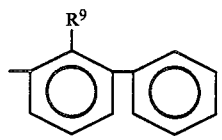

(ii)

wherein $R^9$ is hydrogen, fluorine or methyl.

In another aspect, this invention is directed to a pesticidal composition comprising a pesticidally effective amount of a compound having the formula [I] as described above and a suitable carrier. In other aspects, this invention relates to methods of controlling insects employing such pesticidal compositions.

In yet another aspect, this invention relates to a process for making a compound of the formula:

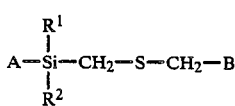

wherein A, $R^1$ and $R^2$ and B are as defined above, which process comprises reacting a halomethyl silane of the formula:

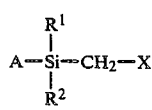

wherein X is chlorine or bromine, and A, $R^1$ and $R^2$ are as defined above; with an alkali metal salt of a mercaptan having the formula:

$HSCH_2B$ wherein B is as defined above.

The compounds of this invention are of the formula:

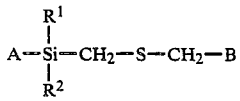

wherein A, B, $R^1$ and $R^2$ are as defined above.
Preferably, $R^1$ and $R^2$ are methyl.
Preferred A substituents include those of the formula:

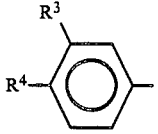

(i)

wherein:
$R^3$ and $R^4$ are the same or different and are hydrogen, $C_1$-$C_4$ alkyl, $C_1$-$C_4$ alkoxy, $C_1$-$C_4$ haloalkyl, $C_1$-$C_4$ haloalkoxy, halogen, phenyl, phenoxy or $C_1$-$C_4$ alkylthio; or
wherein $R^3$ and $R^4$ taken together are methylenedioxy;

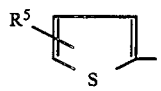

(ii)

wherein $R^5$ is selected from hydrogen, chlorine, bromine, and $C_1$-$C_4$ alkyl; and

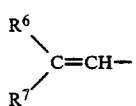

(iii)

wherein $R^6$ and $R^7$ the same or different and are selected from hydrogen, fluorine, chlorine, bromine and trifluoromethyl.

Preferred B substituents include those of the formula:

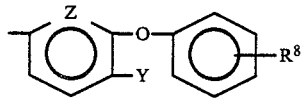

wherein Y, Z and $R^8$ are as defined in formula I above.
Among the more preferred classes of compounds of the present invention are those of the formulae:

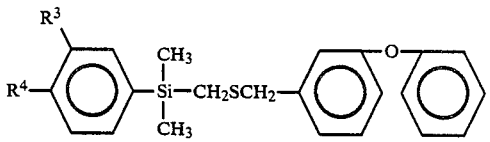

wherein $R^3$ and $R^4$ are the same or different and are hydrogen, $C_1$-$C_4$ alkyl, $C_1$-$C_4$ alkoxy, $C_1$-$C_4$ haloalkoxy or halogen.

Particularly preferred compounds within the scope of this invention include:

(4-ethoxyphenyl)dimethyl(((3-phenoxyphenyl)methyl)thio)methylsilane,
(4-chlorophenyl)dimethyl(((3-phenoxyphenyl)methyl)thio)methylsilane,
Dimethyl(4-methylphenyl)(((3-phenoxyphenyl)methyl)thio)methylsilane,
(4-fluorophenyl)dimethyl(((3-phenoxyphenyl)methyl)thio)methylsilane,
Dimethyl(4-trifluoromethylphenyl)(((3-phenoxyphenyl)methyl)thio)methylsilane,
Dimethyl(3-methylphenyl)(((3-phenoxyphenyl)methyl)thio)methylsilane,
Dimethyl(3-trifluoromethylphenyl)(((3-phenoxyphenyl)methyl)thio)methylsilane,
(4-ethoxyphenyl)dimethyl(((6-phenoxy-2-pyridinyl)methyl)thio)methylsilane,
(4-fluorophenyl)dimethyl(((6-phenoxy-2-pyridinyl)methyl)thio)methylsilane,
(4-chlorophenyl)dimethyl(((6-phenoxy-2-pyridinyl)methyl)thio)methylsilane, and
(4-(difluoromethoxy)phenyl)dimethyl(((3-phenoxyphenyl)methyl)thio)methylsilane.

The compounds of the present invention may be prepared by reacting a halomethyl silane of the formula:

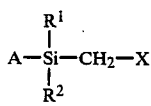

wherein A, $R^1$ and $R^2$ are as previously defined in formula I above, and wherein X is chlorine or bromine; with an alkali metal salt of a mercaptan having the formula:

wherein B is as defined in formula I above.

Such reaction advantageously may be carried out in a reaction medium comprising water and a water-immiscible organic solvent, such as benzene, toluene or hexane.

The reaction may be facilitated by use of any suitable catalyst such as, for example, a quaternary ammonium salt, a quaternary phosphonium salt or a crown ether. Such catalysts suitably function as phase transfer agents when the reaction is carried out in a water/organic solvent reaction medium, as is described in greater detail below. Preferred catalysts include quaternary ammonium salts such as, for example, benzyltriethylammonium chloride, benzyltriethylammonium bromide, cetyltrimethylammonium bromide, methyltributylammonium iodide, tetrabutylammonium chloride, tetraethylammonium chloride and methyltrioctylammonium chloride.

In a preferred method, the reaction of the halomethyl silane with the alkali metal salt of the mercaptan is carried out by adding (i) a solution comprising the halomethyl silane compound and an organic solvent therefor, such as benzene, toluene or hexane, to (ii) a mixture comprising the mercaptan compound, an alkali metal hydroxide, an effective amount of a phase transfer catalyst and an aqueous medium. As indicated, the catalyst may be a quaternary ammonium salt, a quaternary phosphonium salt or a crown ether. The reaction is typically carried out under mixing conditions, at between about 0° C. and about 60° C. Reaction times may vary from an hour or less to a day or more depending upon factors such as reaction batch size, the reaction temperature selected, and the like. However, one skilled in the art may readily determine the optimum reaction time for a given set of reaction parameters by routine experimentation.

The halomethyl silanes employed in the process of this invention may be prepared by known methods, such as those described in "Organosilicon Compounds," C. Eaborn, Academic Press, New York, New York (1960) at page 10.

In like manner, the mercaptan starting materials may be prepared by known methods. Suitable methods of preparation are disclosed in West German Offenlegungsschrift No. 2,944,849, Chemical Abstracts 95, 15017OF (1981), and U.S. Pat. No. 4,238,614.

The compositions of this invention are comprised of (A) a pesticidally effective amount of a compound having the structure indicated in formula I above; and (B) a suitable carrier. Such suitable carriers may be solid or liquid in nature.

Suitable liquid carriers may be comprised of water, alcohols, ketones, phenols, toluene and xylenes. In such formulations, additives conventionally employed in the art may be utilized such as, for example, one or more surface active agents and/or inert diluents, to facilitate handling an application of the resulting pesticide composition.

The pesticidal compositions may alternatively comprise solid carriers taking the form of dusts, granules, wettable powders, pastes, aerosols, emulsions, emulsifiable concentrates, and water-soluble solids.

For example, the pesticidal compounds of this invention may be applied as dusts when admixed with or absorbed onto powdered solid carriers, such as mineral silicates, e.g., mica, talc, pyrophyllite and clays, together with a surface-active dispersing agent so that a wettable powder is obtained which then is applicable directly to the loci to be treated. Alternatively, the powdered solid carrier containing the compound admixed therewith may be dispersed in water to form a suspension for application in such form.

Granular formulations of the compounds, suitable for application by broadcasting, side dressing, oil incorporation or seed treatment, are suitably prepared using a granular or pellitized form of carrier such as granular clays, vermiculite, charcoal or corn cobs.

Alternatively, the pesticidal compounds may be applied in liquids or sprays when utilized in a liquid carrier, such as in a solution comprising a compatible solvent such as acetone, benzene, toluene or kerosene, or as dispersed in a suitable non-solvent medium, for example, water.

Another method of application to loci to be treated in aerosol treatment, for which the compound may be dissolved in an aerosol carrier which is a liquid under pressure but which is a gas at ordinary temperature (e.g., 20° C.) and atmospheric pressure. Aerosol formulations may also be prepared by first dissolving the compound in a less volatile solvent and then admixing the resulting solution with a highly volatile liquid aerosol carrier.

For pesticidal treatment of plants (such term including plant parts), the compounds of the invention preferably are applied in aqueous emulsions containing a surface-active dispersing agent which may be non-ionic, cationic or anionic. Suitable surface-active agents include those known in the art, such as those disclosed in U.S. Pat. No. 2,547,724 (columns 3 and 4). The compounds of the invention may be mixed with such surface-active dispersing agents, with or without an organic solvent, as concentrates for the subsequent addition of water to yield aqueous suspensions of the compounds at desired concentration levels.

In addition, the compounds may be employed with carriers which themselves are pesticidally active, such as insecticides, acaricides, fungicides or bactericides.

It will be understood that the amount of the pesticidally active compound in a given formulation will depend upon the specific pest to be combatted, as well as upon the specific chemical composition and formulation of the compound being employed, the method of applying the compound/formulation and the locus of treatment so that the pesticidally effective amount of the compound may vary widely. Generally, however, concentrations of the compound as the active ingredient in pesticidally effective formulations may range from about 0.1 to about 95 percent by weight. Spray dilutions may be as low as a few parts per million, while at the opposite extreme, full strength concentrates of the compound may be usefully applied by ultra low volume techniques. Concentration per unit area, where plants constitute the loci of treatment, may range between about 0.01 and about 50 pounds per acre, with concentrations of between about 0.01 and about 10 pounds per acre preferably being employed for crops such as corn, tobacco, rice and the like.

To combat pests, sprays of the compounds may be applied to the pests directly and/or to plants upon which they feed or nest. The pesticidally active formulations may also be applied to the soil or other medium in which the pests are present.

Harmful insects and arachnids attack a wide variety of plants, including both ornamental and agricultural plants and inflict damage by consuming roots and/or foliage, withdrawing vital juices from the plants, secreting toxins and often by transmitting diseases. The compounds of the present invention may be advantageously utilized to minimize or prevent such damage. The specific methods of application, as well as the selection and concentration of these compounds will, of course, vary depending upon such circumstance as geographic area, climate, topography, plant tolerance, etc. For specific circumstances, one skilled in the art may readily determine the proper compound, concentration and method of application by routine experimentation.

The compounds of the invention are particularly useful as insecticides and acaricides, for foliar and/or soil application.

EXAMPLES

The following Examples are intended to further illustrate the invention, and are not intended to limit the scope of the invention in any manner whatsoever.

EXAMPLE 1

Preparation of (4-chlorophenyl)dimethyl([[(3-phenoxyphenyl)methyl]thio)methylsilane: Compound No. 3

To a solution of 0.8 grams (19.6 mmoles) of sodium hydroxide, 10 ml. of water and 2 drops of methyltrioctylammonium chloride were added, 4.2 grams (19.6 mmoles) of 3-phenoxybenzenemethanethiol. Such addition occured under agitation at room temperature, in the presence of a nitrogen atmosphere. A solution of 4.3 grams (19.6 mmoles) of chloromethyl-(4-chlorophenyl)-dimethylsilane in 25 ml. of toluene was added to the aqueous mercaptide salt, and the resulting mixture was rapidly stirred at room temperature for 20 hours. The organic layer was separated and washed two times with water and dried ($MgSO_4$). After filtration, was stripped on a rotary evaporator. 7.7 grams of an oil was obtained. This crude product was purified on a Waters ® Prep 500A liquid chromatograph (silica eluting with a 4:1 solvent mixture of hexane/toluene) to give 5.8 grams of (4-chlorophenyl)dimethyl[([(3-phenoxyphenyl)methyl]thio)methyl]silane as a colorless liquid. Nuclear magnetic resonance data for this compound are listed in Table I below.

EXAMPLE 2

Preparation of (4-ethoxyphenyl)dimethyl([[(6-phenoxy-2-pyridinyl)methyl]thio)methylsilane: Compound No. 20

In the manner described in Example 1, 1.8 grams (8.0 mmoles) of (chloromethyl)(4-ethoxyphenyl)dimethylsilane was reacted with 1.7 grams (8.0 mmoles) of 6-phenoxy-2-pyridine methanethiol giving 3.2 grams of a light orange oil. The product was purified on a Waters ® Prep 500A liquid chromatograph (silica gel) eluting with 6 percent ethylacetate in hexane, to yield 2.7 grams of (4-ethoxyphenyl)dimethyl[(((6-phenoxy-2-pyridinyl)methyl)thio)methyl]silane as a clear oil. Analytical data for this product are shown in Table VI.

EXAMPLE 3

Employing the method described in Examples 1 and 2 above, several additional compounds were prepared. The structure of these compounds, along with the nuclear magnetic resonance (NMR) data in $CDCl_3$ is listed in Table I below.

TABLE I $$\underset{R^2}{\overset{R^1}{A-Si-CH_2-S-CH_2}}-\underset{Y}{\overset{Z}{\diagdown}}X-\bigcirc$$

| Compound No. | A | R¹ | R² | X | Y | Z | NMR δ CDCl₃ (ppm) |
|---|---|---|---|---|---|---|---|
| 1 | C₂H₅O—⟨phenyl⟩— | CH₃ | CH₃ | O | H | CH | 0.32(s, 6H), 1.34(t, 3H), 1.80(s, 2H), 3.56(s, 2H), 3.95(q, 2H), 6.6–7.6 (m, 13H) |
| 2 | ⟨phenyl⟩— | CH₃ | CH₃ | O | H | CH | 0.32(s, 6H), 1.82(s, 2H), 3.53(s, 2H), 6.6–7.6 (m, 14H) |
| 3 | Cl—⟨phenyl⟩— | CH₃ | CH₃ | O | H | CH | 0.32(s, 6H), 1.82(s, 2H), 3.55(s, 2H), 6.6–7.5 (m, 13H) |
| 4 | CH₃O—⟨phenyl⟩— | CH₃ | CH₃ | O | H | CH | 0.30(s, 6H), 1.78(s, 2H), 3.51(s, 2H), 3.64(s, 3H), 6.6–7.4(m, 13H) |
| 5 | CH₃—⟨phenyl⟩— | CH₃ | CH₃ | O | H | CH | 0.31(s, 6H), 1.79(s, 2H), 2.25(s, 3H), 3.50(s, 2H), 6.6–7.4(m, 13H) |
| 6 | (CH₃)₃C—⟨phenyl⟩— | CH₃ | CH₃ | O | H | CH | 0.32(s, 6H), 1.29(s, 9H), 1.81(s, 2H), 3.53(s, 2H), 6.6–7.5(m, 13H) |
| 7 | F—⟨phenyl⟩— | CH₃ | CH₃ | O | H | CH | 0.30(s, 6H), 1.81(s, 2H), 3.54(s, 2H), 6.7–7.6 (m, 13H) |
| 8 | CH₃S—⟨phenyl⟩— | CH₃ | CH₃ | O | H | CH | 0.30(s, 6H), 1.81(s, 2H), 2.36(s, 3H), 3.55(s, 2H), 6.7–7.5(m, 13H) |
| 9 | CF₃—⟨phenyl⟩— | CH₃ | CH₃ | O | H | CH | 0.34(s, 6H), 1.84(s, 2H), 3.57(s, 2H), 6.7–7.4 (m, 9H), 7.53(s, 4H) |
| 10 | ⟨phenyl⟩—⟨phenyl⟩— | CH₃ | CH₃ | O | H | CH | 0.35(s, 6H), 1.85(s, 2H), 3.52(s, 2H), 6.7–7.6 (m, 18H) |
| 11 | ⟨phenyl⟩—O—⟨phenyl⟩— | CH₃ | CH₃ | O | H | CH | 0.31(s, 6H), 1.80(s, 2H), 3.52(s, 2H), 6.6–7.5 (m, 18H) |
| 12 | 2-Cl-⟨phenyl⟩— | CH₃ | CH₃ | O | H | CH | 0.31(s, 6H), 1.80(s, 2H), 3.52(s, 2H), 6.7–7.5 (m, 13H) |

TABLE I-continued $$A-\underset{\underset{R^2}{|}}{\overset{\overset{R^1}{|}}{Si}}-CH_2-S-CH_2-\underset{Y}{\overset{Z}{\bigcirc}}X-\bigcirc$$

| Compound No. | A | $R^1$ | $R^2$ | X | Y | Z | NMR δ CDCl₃ (ppm) |
|---|---|---|---|---|---|---|---|
| 13 | CH₃—⌬— | CH₃ | CH₃ | O | H | CH | 0.32(s, 6H), 1.81(s, 2H), 2.27(s, 3H), 3.53(s, 2H), 6.6–7.4(m, 13H) |
| 14 | C₂H₅—⌬— | CH₃ | CH₃ | O | H | CH | 0.33(s, 6H), 1.19(t, 3H), 1.82(s, 2H), 2.60(q, 2H), 3.54(s, 2H), 6.7–7.5 (m, 13H) |
| 15 | CH₃, F—⌬— | CH₃ | CH₃ | O | H | CH | 0.30(s, 6H), 1.81(s, 2H), 2.22(s, 3H), 3,55(s, 2H), 6.7–7.4(m, 12H) |
| 16 | Br—⌬— | CH₃ | CH₃ | O | H | CH | 0.30(s, 6H), 1.80(s, 2H), 3.52(s, 2H), 6.7–7.5 (m, 13H) |
| 17 | CF₃—⌬— | CH₃ | CH₃ | O | H | CH | 0.35(s, 6H), 1.85(s, 2H), 3.55(s, 2H), 6.7–7.8 (m, 13H) |
| 18 | Br—⟨S⟩— | CH₃ | CH₃ | O | H | CH | 0.33(s, 6H), 1.82(s, 2H), 3.59(s, 2H), 6.7–7.5 (m, 11H) |
| 19 | ⟨S⟩— | CH₃ | CH₃ | O | H | CH | 0.35(s, 6H), 1.85(s, 2H), 3.56(s, 2H), 6.7–7.6 (m, 12H) |
| 20 | C₂H₅O—⌬— | CH₃ | CH₃ | O | H | N | 0.30(s, 6H), 1.35(t, 3H), 1.93(s, 2H), 3.60(s, 2H), 3.98(q, 2H), 6.5–7.7 (m, 12H) |
| 21 | CH₃—⌬— | CH₃ | CH₃ | O | H | N | 0.30(s, 6H), 1.92(s, 2H), 2.28(s, 3H), 3.59(s, 2H), 6.5–7.7(m, 12H) |
| 22 | F—⌬— | CH₃ | CH₃ | O | H | N | 0.30(s, 6H), 1.93(s, 2H), 3.58(s, 2H), 6.5–7.7 (m, 12H) |
| 23 | (CH₃)₃C—⌬— | CH₃ | CH₃ | O | H | N | 0.30(s, 6H), 1.30(s, 9H), 1.94(s, 2H), 3.62(s, 2H), 6.5–7.7(m, 12H) |

TABLE I-continued $$A-\underset{\underset{R^2}{|}}{\overset{\overset{R^1}{|}}{Si}}-CH_2-S-CH_2-\underset{Y}{\overset{Z}{\diagup}}\diagdown_X-\bigcirc$$

| Compound No. | A | R¹ | R² | X | Y | Z | NMR δ CDCl₃ (ppm) |
|---|---|---|---|---|---|---|---|
| 24 | Cl-⟨phenyl⟩- | CH₃ | CH₃ | O | H | N | 0.30(s, 6H), 1.93(s, 2H), 3.58(s, 2H), 6.5–7.7 (m, 12H) |
| 25 | F₂CHO-⟨phenyl⟩- | CH₃ | CH₃ | O | H | CH | 0.31(s, 6H), 1.83(s, 2H), 3.58(s, 2H), 6.45(t, J$_{HF}$ = 74Hz, 1H), 6.7–7.6 (m, 13H) |
| 26 | F₂CHO-⟨phenyl⟩- | CH₃ | CH₃ | O | H | N | 0.31(s, 6H), 1.92(s, 2H), 3.58(s, 2H), 6.39(t, J$_{HF}$ = 73Hz, 1H), 6.5–7.5 (m, 12H) |

EXAMPLE 4

Employing a process similar to that described in Examples 1 and 2, the compounds listed in Table II are prepared.

TABLE II $$A-\underset{\underset{R^2}{|}}{\overset{\overset{R^1}{|}}{Si}}-CH_2-S-CH_2-\underset{Y}{\overset{Z}{\diagup}}\diagdown_X-\bigcirc$$

| Compound No. | A | R¹ | R² | X | Y | Z |
|---|---|---|---|---|---|---|
| 27 | C₂H₅O-⟨phenyl⟩- | CH₃ | CH₃ | O | F | CH |
| 28 | F-⟨phenyl⟩- | CH₃ | CH₃ | O | F | CH |
| 29 | Cl-⟨phenyl⟩- | CH₃ | CH₃ | O | F | CH |
| 30 | CH₃-⟨phenyl⟩- | CH₃ | CH₃ | O | F | CH |
| 31 | (CH₃)₃C-⟨phenyl⟩- | CH₃ | CH₃ | O | F | CH |
| 32 | F₂CHO-⟨phenyl⟩- | CH₃ | CH₃ | O | F | CH |

EXAMPLE 5

Employing a process similar to that described in Examples 1 and 2, the compounds listed in Table III are prepared:

TABLE III $$A-\underset{\underset{R^2}{|}}{\overset{\overset{R^1}{|}}{Si}}-CH_2-S-CH_2-\overset{R^9}{\underset{}{\bigcirc}}-\bigcirc$$

| Compound No. | A | R¹ | R² | R⁹ |
|---|---|---|---|---|
| 33 | C₂H₅O-⟨phenyl⟩- | CH₃ | CH₃ | H |
| 34 | C₂H₅O-⟨phenyl⟩- | CH₃ | CH₃ | CH₃ |
| 35 | Cl-⟨phenyl⟩- | CH₃ | CH₃ | CH₃ |

TABLE III-continued $$A-\underset{\underset{R^2}{|}}{\overset{\overset{R^1}{|}}{Si}}-CH_2-S-CH_2-\underset{}{\bigcirc}\underset{}{\overset{R^9}{\bigcirc}}$$

| Compound No. | A | R¹ | R² | R⁹ |
|---|---|---|---|---|
| 36 | F₂CHO—⟨◯⟩— | CH₃ | CH₃ | CH₃ |
| 37 | CH₃—⟨◯⟩— | CH₃ | CH₃ | H |
| 38 | F—⟨◯⟩— | CH₃ | CH₃ | CH₃ |
| 39 | C₂H₅O—⟨◯⟩— | CH₃ | CH₃ | F |
| 40 | Cl—⟨◯⟩— | CH₃ | CH₃ | H |

EXAMPLE 4

The organosilane compounds of this invention were tested for their insecticidal and acaricidal efficacy employing the following procedures:

(A) Southern Corn Rootworm Test

Stock solutions of the compounds were prepared at 6000 ppm (parts per million) by dissolving 0.6 gram of the compound to be tested in 10 ml of acetone and adding 100 ml of water plus 4 drops of ethoxylated sorbitan monolaurate, a wetting agent. Test formulations having a concentration of 500 ppm were prepared by diluting the stock solution with distilled water.

Five ml of the dilution is pipetted onto a paper towel, which is inserted into a Ziploc ® plastic bag. Two corn seedlings are also soaked in the chemical preparation and placed in the plastic bag. Bags are held for 18 hours before being loaded with 5 corn rootworm (*Diabrotica undecimpunctata*) larvae. After six days, the number of live larvae are noted and the percent control is calculated.

(B) Mite Test

Test formulations were prepared having a 1,000 ppm concentration. Cowpeas, in the first primary leaf stage, were used in the test. Two plants per pot (one primary leaf each) were used for each replicate; two replicates were used for each compound tested. The plants were sprayed with the dispersions using a spray atomizer to thoroughly drench the foliage.

One day following treatment, a circle of tree tanglefoot was placed on the upper surface of the treated leaves and adult mites, (*Tetranychus urticate* Koch) were transferred into this confinement.

Six days following infestation with mites, the plants were examined for adult live mites remaining on the leaves. On an estimated basis in comparison with the number of living mites on the control plants, the percent control was determined.

(C) Rice Planthopper Test

Test formulations of 1000 ppm suspensions were prepared. Two rice seedling plants were treated with each formulation by spraying with a spray atomizer. Ten adult rice planthoppers, (*Sogatodes oryzicola*) were placed on plants in each pot one day following treatment. The surviving planthoppers were counted after five days to determine the percent control.

(D) Tobacco Budworm Diet Test

The stock solution was diluted with distilled water to a concentration of 3000 ppm. Two-tenths ml of the diluted formulation was pipetted onto the surface of 5 grams of a synthetic diet mixture held in partially filled cells of a plastic jelly tray. Five cells were treated with the chemical dilution in this manner.

Following treatment, a third instar larva of the tobacco budworm (*Heliothis virescens*) was placed in each cell. At the end of one and two weeks, trays were examined and the percent control was determined.

(E) Boll Weevil Test

Test formulations were prepared at 1000 ppm. Two cotton seedling plants were treated with each formulation by spraying with a spray atomizer. Five adult boll weevils (*Anthonomous grandis*) were placed on plants in each pot one day following treatment. The surviving weevils were counted after five days to determine the percent control.

The results of such testing, as percent control, are summarized in Table III below.

TABLE IV

| Compound No. | Corn Rootworm | Mite | Rice Plant hopper | Tobacco Budworm | Weevil |
|---|---|---|---|---|---|
| 1 | 63 | 0 | 90 | 100 | 90 |
| 2 | 100 | 0 | 0 | 100 | 6 |
| 3 | 100 | 0 | 60 | 100 | 41 |
| 4 | 33 | 70 | 100 | 100 | 67 |
| 5 | 100 | 70 | 100 | 100 | 44 |
| 6 | 17 | 90 | 50 | 60 | 0 |
| 7 | 100 | 0 | 100 | 100 | 33 |
| 8 | 100 | 0 | 100 | 80 | 56 |
| 9 | 100 | 0 | 100 | 100 | 44 |
| 10 | 40 | 0 | 0 | 0 | —* |
| 11 | 100 | 70 | 0 | 0 | 18 |
| 12 | 100 | 0 | 95 | 100 | 90 |
| 13 | 75 | 0 | 50 | 100 | 6 |
| 14 | 100 | 50 | 100 | 100 | 100 |
| 15 | 100 | 80 | 100 | 100 | 100 |
| 16 | 100 | 90 | 100 | 100 | 100 |
| 17 | 100 | 0 | 70 | 100 | 58 |
| 18 | 71 | 0 | 100 | 100 | 68 |
| 19 | 14 | 0 | 70 | 80 | 39 |
| 20 | 100 | 70 | 0 | 100 | 12 |
| 21 | 100 | 0 | 0 | 80 | 50 |
| 22 | 100 | 0 | 95 | 100 | 12 |
| 23 | 60 | 0 | 100 | 100 | 12 |
| 24 | 100 | 0 | 95 | 100 | 12 |
| 25 | 100 | 100 | 100 | 100 | —* |
| 26 | 100 | 100 | 100 | 100 | —* |

*—indicates not tested.

What is claimed is:

1. A compound of the formula:

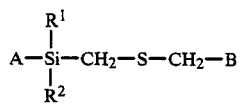

wherein:

$R_1$ and $R_2$ may be the same or different, and are lower alkyl;

A is selected from radicals having the structure:

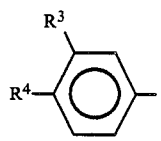 (i)

wherein $R^3$ and $R^4$ are the same or different and are hydrogen $C_1$-$C_4$ alkyl, $C_1$-$C_4$ alkoxy, $C_1$-$C_4$ haloalkyl, $C_1$-$C_4$ haloalkoxy, halo, phenyl, phenoxy or $C_1$-$C_4$ alkylthio; or wherein $R^3$ and $R^4$ taken together are methylenedioxy;

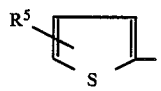 (ii)

wherein $R^5$ is hydrogen, chlorine, bromine or $C_1$-$C_4$ alkyl; and

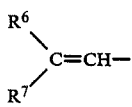 (iii)

wherein $R^6$ and $R^7$ are the same or different and are hydrogen, fluorine, chlorine, bromine or trifluoromethyl; and B is selected from radicals having the structure:

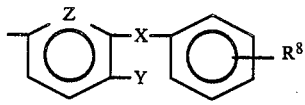 (i)

wherein:

X is oxygen, NH, $CH_2$, carbonyl or sulfur;
Y is hydrogen, fluorine, chlorine or methyl;
Z is CH or nitrogen; and
$R^8$ is hydrogen, fluorine, chlorine or bromine; and

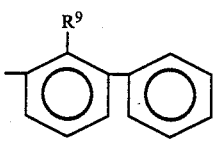 (ii)

wherein $R^9$ is hydrogen, fluorine or methyl.

2. A compound in accordance with claim 1 wherein $R^1$ and $R^2$ are methyl;

A is selected from radicals having the structure:

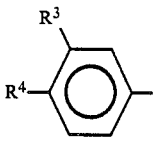 (i)

wherein $R^3$ and $R^4$ are the same or different and are hydrogen $C_1$-$C_4$ alkyl, $C_1$-$C_4$ alkoxy, $C_1$-$C_4$ haloalkyl, $C_1$-$C_4$ haloalkoxy, halo, phenyl, phenoxy or $C_1$-$C_4$ alkylthio; or wherein $R^3$ and $R^4$ taken together are methylenedioxy;

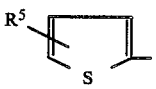 (ii)

wherein $R^5$ is hydrogen, chlorine, bromine or $C_1$-$C_4$ alkyl; and

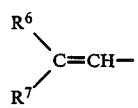 (iii)

wherein $R^6$ and $R^7$ are the same or different and are hydrogen, fluorine, chlorine, bromine or trifluoromethyl; and B is selected from radicals having the structure:

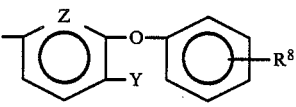

wherein $R^8$, Y and Z are as defined in claim 1.

3. A compound in accordance with claim 1 wherein:
$R^1$ and $R^2$ are methyl;
B is a radical having the structure

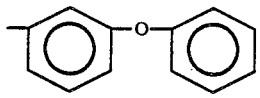

and A is a radical having the formula:

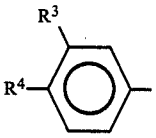

wherein $R^3$ and $R^4$ are the same or different and are hydrogen $C_1$-$C_4$ alkyl, $C_1$-$C_4$ alkoxy, $C_1$-$C_4$ haloalkoxy or halogen.

4. A compound in accordance with claim 1 wherein said compound is selected from the group consisting of:
(4-ethoxyphenyl)dimethyl(((3-phenoxyphenyl)methyl)thio)methylsilane, (4-chlorophenyl)dimethyl(((3-phenoxyphenyl)methyl)thio)methylsilane,
Dimethyl(4-methylphenyl)(((3-phenoxyphenyl)methyl)thio)methylsilane,
(4-fluorophenyl)dimethyl(((3-phenoxyphenyl)methyl)thio)methylsilane,
Dimethyl(4-trifluoromethylphenyl)(((3-phenoxyphenyl)methyl)thio)methylsilane,
Dimethyl(3-methylphenyl)(((3-phenoxyphenyl)methyl)thio)methylsilane,
Dimethyl(3-trifluoromethylphenyl)(((3-phenoxyphenyl)methyl)thio)methylsilane,
(4-ethoxyphenyl)dimethyl(((6-phenoxy-2-pyridinyl)methyl)thio)methylsilane,
(4-fluorophenyl)dimethyl(((6-phenoxy-2-pyridinyl)methyl)thio)methylsilane,
(4-chlorophenyl)dimethyl(((6-phenoxy-2-pyridinyl)methyl)thio)methylsilane, and
(4-(difluoromethoxy)phenyl)dimethyl(((3-phenoxyphenyl)methyl)thio)methylsilane.

5. A pesticidal composition comprising:
(A) A insecticidally and acaricidally effective amount of a compound having the formula:

$$A-\underset{\underset{R^2}{|}}{\overset{\overset{R^1}{|}}{Si}}-CH_2-S-CH_2-B$$

wherein:
$R_1$ and $R_2$ may be the same or different, and are lower alkyl;
A is selected from radicals having the structure:

(i) [structure with $R^3$, $R^4$ substituents on phenyl ring]

wherein $R^3$ and $R^4$ are the same or different and are hydrogen $C_1$-$C_4$ alkyl, $C_1$-$C_4$ alkoxy, $C_1$-$C_4$ haloalkyl, $C_1$-$C_4$ haloalkoxy, halo, phenyl, phenoxy or $C_1$-$C_4$ alkylthio; or
wherein $R^3$ and $R^4$ taken together are methylenedioxy;

(ii) [thiophene structure with $R^5$]

wherein $R^5$ is chlorine, bromine or $C_1$-$C_4$ alkyl; and (iii) $\underset{R^7}{\overset{R^6}{\diagdown}}C=CH-$ wherein $R^6$ and $R^7$ are the same or different and are hydrogen, fluorine, chlorine, bromine or trifluoromethyl; and
B is selected from radicals having the structure:

(i) [biphenyl structure with Z, X, Y, $R^8$]

wherein:
X is oxygen, NH, $CH_2$, carbonyl or sulfur;
Y is hydrogen, fluorine, chlorine or methyl;
Z is CH or nitrogen; and
$R^8$ is hydrogen, fluorine, chlorine or bromine; and (ii) [naphthalene-like structure with $R^9$]

wherein $R^9$ is hydrogen, fluorine or methyl; and
(B) a suitable carrier.

6. A composition in accordance with claim 5 wherein in component (A):
$R^1$ and $R^2$ are methyl;
A is selected from radicals having the structure:

(i) [phenyl with $R^3$, $R^4$]

wherein $R^3$ and $R^4$ are the same or different and are hydrogen $C_1$-$C_4$ alkyl, $C_1$-$C_4$ alkoxy, $C_1$-$C_4$ haloalkyl, $C_1$-$C_4$ haloalkoxy, halo, phenyl, phenoxy or $C_1$-$C_4$ alkylthio; or
wherein $R^3$ and $R^4$ taken together are methylenedioxy;

(ii) [thiophene with $R^5$]

wherein $R^5$ is hydrogen, chlorine, bromine or $C_1$-$C_4$ alkyl; and (iii) $\underset{R^7}{\overset{R^6}{\diagdown}}C=CH-$ wherein $R^6$ and $R^7$ are the same or different and are hydrogen, fluorine, chlorine, bromine or trifluoromethyl; and
B is selected from radicals having the structure:

[biphenyl ether structure with Z, O, Y, $R^8$]

wherein $R^8$, Y and Z are as defined in claim 1.

7. A composition in accordance with claim 6 wherein:

$R^1$ and $R^2$ are methyl;
B is a radical having the structure

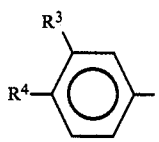

and A is a radical having the formula:

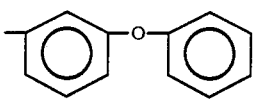

wherein $R^3$ and $R^4$ are the same or different and are hydrogen $C_1$–$C_4$ alkyl, $C_1$–$C_4$ alkoxy, $C_1$–$C_4$ haloalkoxy or halogen.

8. A composition in accordance with claim 5 wherein component (B) is a liquid carrier.

9. A composition in accordance with claim 8 wherein the liquid carrier contains at least one member of the group consisting of water, alcohols, ketones, phenols, toluene and xylene.

10. A composition in accordance with claim 5 wherein component (B) is a solid carrier.

11. A composition in accordance with claim 10 wherein component (B) is selected from at least one member of the group consisting of mineral silicates, charcoal and corn cobs.

12. A composition in accordance with claim 5 wherein component (A) is selected from the group consisting of:
- (4-ethoxyphenyl)dimethyl(((3-phenoxyphenyl)methyl)thio)methylsilane,
- (4-chlorophenyl)dimethyl(((3-phenoxyphenyl)methyl)thio)methylsilane,
- Dimethyl(4-methylphenyl)(((3-phenoxyphenyl)methyl)thio)methylsilane,
- (4-fluorophenyl)dimethyl(((3-phenoxyphenyl)methyl)thio)methylsilane,
- Dimethyl(4-trifluoromethylphenyl)(((3-phenoxyphenyl)methyl)thio)methylsilane,
- Dimethyl(3-methylphenyl)(((3-phenoxyphenyl)methyl)thio)methylsilane,
- Dimethyl(3-trifluoromethylphenyl)(((3-phenoxyphenyl)methyl)thio)methylsilane,
- (4-ethoxyphenyl)dimethyl(((6-phenoxy-2-pyridinyl)methyl)thio)methylsilane,
- (4-fluorophenyl)dimethyl(((6-phenoxy-2-pyridinyl)methyl)thio)methylsilane,
- (4-chlorophenyl)dimethyl(((6-phenoxy-2-pyridinyl)methyl)thio)methylsilane, and
- (4-difluoromethoxy)phenyl)dimethyl(((3-phenoxyphenyl)methyl)thio)methylsilane.

13. A method of controlling insects comprising applying to plants an insecticidally effective amount of a compound of the formula:

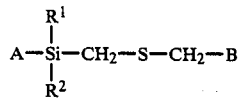

wherein:

$R_1$ and $R_2$ may be the same or different, and are lower alkyl;

A is selected from radicals having the structure:

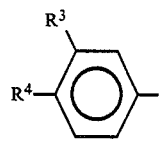 (i)

wherein $R^3$ and $R^4$ are the same or different and are hydrogen $C_1$–$C_4$ alkyl, $C_1$–$C_4$ alkoxy, $C_1$–$C_4$ haloalkyl, $C_1$–$C_4$ haloalkoxy, halo, phenyl, phenoxy or $C_1$–$C_4$ alkylthio; or
wherein $R^3$ and $R^4$ taken together are oxydialkylene;

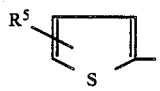 (ii)

wherein $R^5$ is hydrogen, chlorine, bromine or $C_1$–$C_4$ alkyl; and

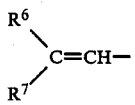 (iii)

wherein $R^6$ and $R^7$ are the same or different and are hydrogen, fluorine, chlorine, bromine or trichloromethyl; and B is selected from radicals having the structure:

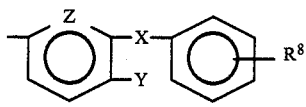 (i)

wherein:
X is oxygen, NH, $CH_2$, carbonyl or sulfur;
Y is hydrogen, fluorine, chlorine or methyl;
Z is CH or nitrogen; and
$R^8$ is hydrogen, fluorine, chlorine or bromine; and

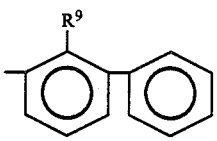 (ii)

wherein $R^9$ is hydrogen, fluorine or methyl.

14. A method in accordance with claim 13 wherein $R^1$ and $R^2$ are methyl;
A is selected from radicals having the structure:

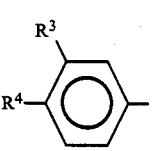 (i)

wherein $R^3$ and $R^4$ are the same or different and are hydrogen $C_1$–$C_4$ alkyl, $C_1$–$C_4$ alkoxy, $C_1$–$C_4$ haloalkyl, $C_1$-$C_4$ haloalkoxy, halo, phenyl, phenoxy or $C_1$-$C_4$ alkylthio; or wherein $R^3$ and $R^4$ taken together are methylenedioxy;

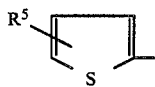 (ii)

wherein $R^5$ is hydrogen, chlorine, bromine or $C_1$-$C_4$ alkyl; and

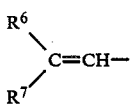 (iii)

wherein $R^6$ and $R^7$ are the same or different and are hydrogen, fluorine, chlorine, bromine trifluoromethyl; and B is selected from radicals having the structure:

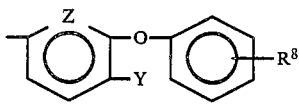

wherein $R^8$, Y and Z are as defined in claim 1.

15. A method in accordance with claim 13 wherein:
$R^1$ and $R^2$ are methyl;
B is a radical having the structure

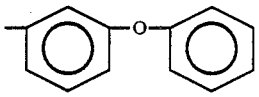

and A is a radical having the formula:

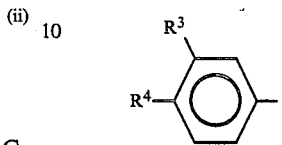

wherein $R^3$ and $R^4$ are the same or different and are hydrogen $C_1$-$C_4$ alkyl, $C_1$-$C_4$ alkoxy, $C_1$-$C_4$ haloalkoxy or halogen.

16. A method in accordance with claim 13 wherein said compound is selected from the group consisting of:
(4-ethoxyphenyl)dimethyl(((3-phenoxyphenyl)methyl)thio)methylsilane,
(4-chlorophenyl)dimethyl(((3-phenoxyphenyl)methyl)thio)methylsilane,
Dimethyl(4-methylphenyl)(((3-phenoxyphenyl)methyl)thio)methylsilane,
(4-fluorophenyl)dimethyl(((3-phenoxyphenyl)methyl)thio)methylsilane,
Dimethyl(4-trifluoromethylphenyl)(((3-phenoxyphenyl)methyl)thio)methylsilane,
Dimethyl(3-methylphenyl)(((3-phenoxyphenyl)methyl)thio)methylsilane,
Dimethyl(3-trifluoromethylphenyl)(((3-phenoxyphenyl)methyl)thio)methylsilane,
(4-ethoxyphenyl)dimethyl(((6-phenoxy-2-pyridinyl)methyl)thio)methylsilane,
(4-fluorophenyl)dimethyl(((6-phenoxy-2-pyridinyl)methyl)thio)methylsilane,
(4-chlorophenyl)dimethyl(((6-phenoxy-2-pyridinyl)methyl)thio)methylsilane, and
(4-difluoromethoxy)phenyl)dimethyl(((3-phenoxyphenyl)methyl)thio)methylsilane.

* * * * *